US008113206B2

(12) United States Patent
Roettger et al.

(10) Patent No.: US 8,113,206 B2
(45) Date of Patent: Feb. 14, 2012

(54) ORAL APPLIANCES WITH MAJOR CONNECTORS AND METHODS FOR MANUFACTURE

(75) Inventors: Mark Roettger, Lake Elmo, MN (US); Robert C. Molhoek, Edina, MN (US); Jon D. Kittelsen, Stillwater, MN (US); Henry D. Cross, III, Murrells Inlet, SC (US); Paul A. Broadbent, Mill Valley, CA (US); Paul L. Bradshaw, Perbroke Pines, FL (US); Paul C. Belvedere, Edina, MN (US); William L. Ballanoff, Davie, FL (US)

(73) Assignee: Bite Tech, Inc., Minneapolis, MN (US)

( * ) Notice: Subject to any disclaimer, the term of this patent is extended or adjusted under 35 U.S.C. 154(b) by 0 days.

(21) Appl. No.: 12/484,223

(22) Filed: Jun. 14, 2009

(65) Prior Publication Data
US 2009/0308403 A1  Dec. 17, 2009

Related U.S. Application Data

(63) Continuation-in-part of application No. 10/460,886, filed on Jun. 12, 2003, which is a continuation-in-part of application No. 09/657,421, filed on Sep. 8, 2000, now Pat. No. 6,626,180.

(60) Provisional application No. 61/132,590, filed on Jun. 19, 2008.

(51) Int. Cl.
*A61F 5/37* (2006.01)
*A61F 5/56* (2006.01)
*A61F 11/00* (2006.01)
*A61C 5/14* (2006.01)

(52) U.S. Cl. ........ 128/861; 128/846; 128/848; 128/857; 128/862; 433/6

(58) Field of Classification Search ........... 128/846, 128/848, 857, 859, 861, 862; 433/6
See application file for complete search history.

(56) References Cited

U.S. PATENT DOCUMENTS

| 4,671,766 | A | * | 6/1987 | Norton | 433/6 |
|---|---|---|---|---|---|
| 5,299,936 | A | * | 4/1994 | Ueno | 433/71 |
| 5,386,821 | A | * | 2/1995 | Poterack | 128/200.26 |
| 5,836,761 | A | * | 11/1998 | Belvedere et al. | 433/6 |
| 5,879,155 | A | * | 3/1999 | Kittelsen | 433/6 |
| 6,152,138 | A | * | 11/2000 | Brown et al. | 128/859 |
| 6,164,278 | A | * | 12/2000 | Nissani | 128/848 |
| 6,200,133 | B1 | * | 3/2001 | Kittelsen | 433/6 |
| 6,371,758 | B1 | * | 4/2002 | Kittelsen | 433/6 |
| 6,978,786 | B2 | * | 12/2005 | Sabbagh | 128/859 |
| 2006/0011204 | A1 | * | 1/2006 | Maher | 128/861 |

* cited by examiner

*Primary Examiner* — Patricia Bianco
*Assistant Examiner* — Brandon Jackson
(74) *Attorney, Agent, or Firm* — Clise, Billion & Cyr, P.A.; Ben Armitage

(57) ABSTRACT

Oral appliances adapted to for spacing the occlusal surfaces of the teeth of a user are disclosed. The oral appliances have a major connector interconnecting a first bite pad and a second bite pad. The first bite pad can include a first spacer and the second bite pad can include a second spacer that are configured to maintain the spacing of the occlusal surfaces of opposing teeth of a user during clenching or upon an impact to the jaw. Methods for the manufacture of composite oral appliances are also disclosed. The methods include forming a composite oral appliance over a model of a user's mouth.

6 Claims, 10 Drawing Sheets

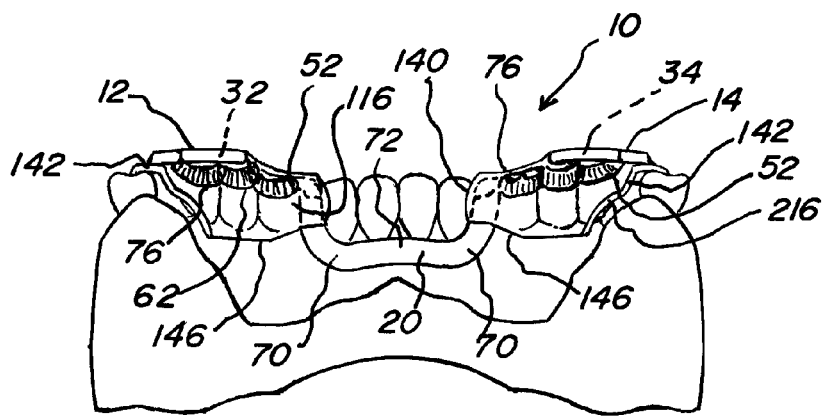
Fig. 9A
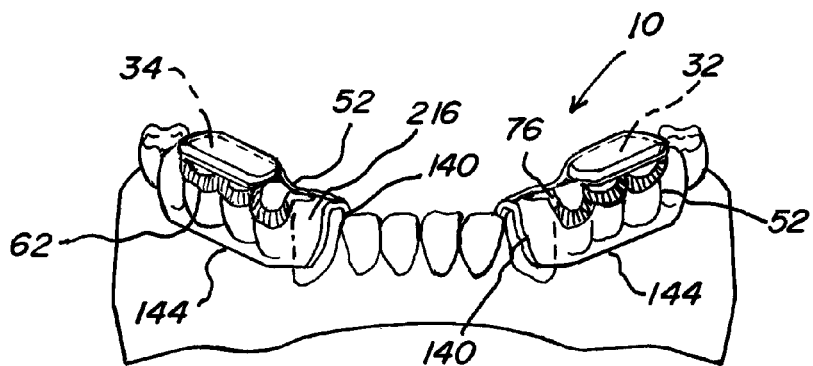
Fig. 9B
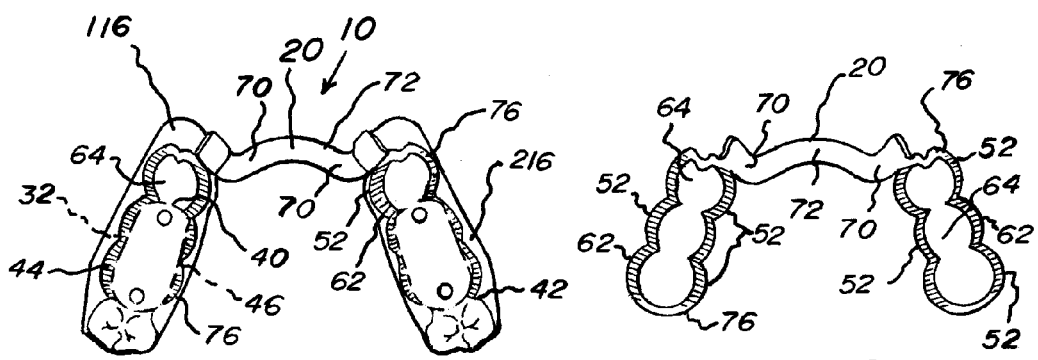
Fig. 9C
Fig. 9D

ORAL APPLIANCES WITH MAJOR CONNECTORS AND METHODS FOR MANUFACTURE

CROSS-REFERENCE TO RELATED APPLICATIONS

The present patent application is a continuation-in-part of U.S. patent application Ser. No. 10/460,886, filed on Jun. 12, 2003 and now published as U.S. Pat. Pub. No. 2004/0250817, which is a continuation-in-part of U.S. patent application Ser. No. 09/657,421, filed on Sep. 8, 2000 and now issued as U.S. Pat. No. 6,626,180 each of which is hereby incorporated by reference into the present disclosure. In addition, the present application claims benefit and priority to U.S. Prov. Pat. Appl. No. 61/132,590, filed on Jun. 19, 2008 which is hereby incorporated by reference into the present disclosure.

BACKGROUND OF THE INVENTION

1. Summary of the Invention

The present inventions relate to mouthpieces and, more particularly, to oral devices for spacing the occlusal surfaces of the teeth of a user.

2. Description of the Related Art

Stress is a normal physiologic response and can be beneficial, maintaining alertness, focus, and efficiency. However, the body can become overloaded when stress becomes excessive (such as during the "fight or flight response") and both performance and health may be adversely affected. Teeth clench in response to elevated stress levels. This clenching mechanism may complete a circuit, as it were, and may signal the brain to begin a complex series of responses in the hypothalamic-pituitary-adrenal (HPA) axis. The HPA axis is a feedback loop signaling the release of hormones and affects various parts of the body. When someone is faced with a stressful situation, the hypothalamus releases the corticotropin-releasing hormone (CRH), which activates the pituitary gland to release adrenocorticotropin into the bloodstream. This triggers the adrenal glands to release epinephrine (adrenaline), norepinephrine (noradrenaline), and cortisol, all enabling the body's stress response. Epinephrine increases blood pressure, reaction time, and heart rate, and sends blood to the muscles. Cortisol releases glucose to supply the brain and muscles with immediate energy. The HPA axis communicates with regions of the brain, including the limbic system, which controls motivation and mood. It also communicates with the hippocampus, which has a vital role in memory formation, mood, and motivation. Other affected areas include body temperature, appetite, and pain control. Stress will also shut down hormonal systems, which affects growth, metabolism, and immunity. This serves as a useful short-term solution when the body must marshal its energies to confront or run from the source of stress. However, stress's interference outlives its usefulness and becomes detrimental when chronic.

Cortisol, the "stress hormone," is essentially the trigger for adrenaline. Cortisol belongs to a class of hormones called glucocorticoids, which affect almost every organ and tissue in the body. Scientists believe cortisol has hundreds of positive effects in the body but Cortisol's most important role may be to help the body respond properly to stress. Cortisol helps maintain blood pressure and cardiovascular function and is essential to normal functioning but needs to remain in proper balance. At excessively high levels, particularly for long periods, the whole endocrine system is affected negatively. High cortisol levels limit peripheral vision, decrease metabolism, cause fatigue, reduce muscle-building, and suppress the immune system. The results of tests showing, among other benefits, a significant increase in endurance as well as a marked reduction in Cortisol during stress. Therefore, a need exists for an apparatus that can interrupt the fight-or-flight signal by preventing the completion of the clenching mechanism.

Similar to other forms of stress, the natural inclination to clench the jaw during physical exertion is typically difficult to avoid. There are various theories as to why individuals clench their teeth in a wide variety of circumstances. One theory is that this is a primal reflex designed to protect the jaw from displacement or fracture. People still instinctively clench their teeth during aggression or physical activity. Accordingly, a need exists for an apparatus that may inhibit or prevent this clenching from completing "the circuit" that could signal the brain to begin a complex series of responses in the hypothalamic-pituitary-adrenal (HPA) axis.

It is also well recognized that the birthing process creates a tremendous amount of physiological and psychological stress upon the mother. The actual birthing process is very analogous to athletes as women about to give birth may very well clench their teeth during the exertion of labor. Therefore, a need exists for an apparatus that can interrupt the resulting physiological response by preventing the completion of the clenching mechanism.

It is also well recognized that military service generates a tremendous amount of physiological and psychological stress in the soldiers. This stress may result in regular clenching of the soldiers' teeth as they during the exertion of labor. This clenching can cause a number of changes that can detrimentally affect their physiology, psychology and judgment. Therefore, a need exists for an apparatus that preventing the completion of the clenching mechanism.

To be useful, an apparatus that prevents the completion of the clenching mechanism should be comfortable and unobtrusive and should not impede breathing or speaking to promote its use. However, many current designs for devices worn in the mouth have significant visual clues that they are being worn. They also frequently impede speech causing many users to have a lisp when they speak. Further, certain designs can significantly impede breathing through the mouth. Therefore, a need exists for apparatus that is both comfortable and unobtrusive when worn by a user.

For adequate fit and comfort, custom manufacture of certain oral appliance designs based on models of the users' teeth can be necessary. However, custom manufacture can be laborious and expensive. Therefore, a need exists for simple reproducible methods for manufacturing oral appliances that reduce the time and effort involved in the manufacture of custom oral appliances.

SUMMARY OF THE INVENTION

Apparatus and methods in accordance with the present invention may resolve many of the needs and shortcomings discussed above and will provide additional improvements and advantages as will be recognized by those skilled in the art upon review of the present disclosure.

In certain aspects, an oral appliance in accordance with aspects of the present invention may include: a first body configured to be secured over one or more teeth of a user, the first body comprising a composite structure, the composite structure comprising at least an outer layer secured over an inner layer, the first body further defining at least a first bite pad, the composite structure at the first bite pad comprising at least a first spacer secured between an outer layer secured and an inner layer, the first bite pad in a position to contact at least one of a molar a premolar of user, an inner surface of the inner layer defining an exterior shape of at least a portion of the teeth of a user; a second body configured to be secured over at least some teeth of a user, the second body comprising a composite structure, the composite structure comprising at least an outer layer secured over an inner layer, the second body further defining at least a second bite pad, the composite structure at the second bite pad comprising at least a second spacer secured between an outer layer secured and an inner layer, the second bite pad in a position to contact at least one of a molar and a premolar when worn by the user, an inner surface of the inner layer defining an exterior shape of at least a portion of the teeth of a user; and a major connector defining a first mounting portion and a second mounting portion, the first mounting portion secured to the first body and the second mounting portion secured to the second body.

In certain aspects, an oral appliance in accordance with the present invention may further include: the major connector extending from a buccal edge of the first body and having a first mesial bend and the major connector extending from a buccal edge of the first body and having a second mesial bend, an arch of the major connector extending between the first mesial bend and the second mesial bend with the first mesial bend and the second mesial bend configured to position the arch of the major connector adjacent to one of incisors of the user and the gum line adjacent to the incisors of the user.

In certain aspects, an oral appliance in accordance with the present invention may further include: the major connector extending from a mesial edge of the first body and the major connector extending from a mesial edge of the first body, an arch of the major connector extending between the first body and the second body with the arch of the major connector configured to be positioned adjacent to one of incisors of the user and the gum line adjacent to the incisors of the user.

In certain aspects, a method for manufacturing an oral appliance in accordance with the present invention may include: providing a model of one of an upper set of teeth and a lower set of teeth; forming an inner blank over at least a portion of the model; positioning a first spacer and a second spacer on an upper surface of the inner blank over at least one of a molar and a premolar of the model; forming an outer blank over at least a portion of the model; securing the outer blank over the inner blank to form at least a first bite pad securing at least the first spacer and a second bite pad securing at least a second spacer to relatively secure at least a portion of the outer blank, the first spacer, the second spacer, and the inner blank together as a composite structure; and securing a major connector between the first bite pad and the second bite pad.

In certain aspects, a method for manufacturing a composite oral appliance in accordance with the present invention may further include forming the inner blank by: positioning the model in a forming chamber of a pressure forming apparatus; sealingly engaging an inner blank between the forming chamber and a high pressure chamber of the pressure forming apparatus; and generating a pressure differential between the forming chamber and the high pressure chamber to draw a portion of the blank over the model.

In certain aspects, a method for manufacturing a composite oral appliance in accordance with the present invention may further include forming the outer blank by: sealingly engaging an outer blank between the forming chamber and a high pressure chamber of the pressure forming apparatus; and generating a pressure differential between the forming chamber and the high pressure chamber to draw a portion of the blank over the first spacer and the second spacer and the first blank.

In certain aspects, a method for manufacturing a composite oral appliance in accordance with the present invention may further include: forming a first body including the first spacer and a second body including the second spacer, and the first body secured to the second body by the major connector.

In certain aspects, a method for manufacturing a composite oral appliance in accordance with the present invention may further include: forming a first body including the first spacer and the second body including the second spacer from the composite structure; and securing with the first body secured to the second body with major connector by securing a first retention portion of the major connector within the first body and securing a second retention portion of the major connector within the second body.

In certain aspects, a method for manufacturing an oral appliance in accordance with the present invention may include: providing a model of one of an upper set of teeth and a lower set of teeth; providing an inner material over the surface of at least one of a molar and a premolar of the model; positioning a first spacer and a second spacer on an upper surface of the inner material over at least one of a molar and a premolar on both a left side and a right side of the model; forming an outer blank over at least a portion of the first spacer, the second spacer, the inner material and the model to relatively secure at least a portion of the outer blank, the first spacer, the second spacer, and the inner material together as a composite structure; and securing the major connector in at least one of the inner blank and the inner material.

In certain aspects, a method for manufacturing a composite oral appliance in accordance with the present invention may further include forming the outer blank by: positioning the model in a forming chamber of a pressure forming apparatus; sealingly engaging a first blank between the forming chamber and a high pressure chamber of the pressure forming apparatus; and generating a pressure differential between the forming chamber and the high pressure chamber to form at least a portion of the first blank over the first spacer and the second spacer and the inner material.

In certain aspects, a method for manufacturing a composite oral appliance in accordance with the present invention may further include: forming a first body including the first spacer and a second body including the second spacer, and securing the first body to the second body with the major connector.

BRIEF DESCRIPTION OF THE FIGURES

FIG. 9A illustrates a rear view of an exemplary embodiment of an oral appliance positioned on the lower teeth of a user in accordance with aspects of the present inventions;

FIG. 9B illustrates a front view of an exemplary embodiment of an oral appliance positioned on the lower teeth of a user in accordance with aspects of the present inventions;

FIG. 9C illustrates a bottom view of an exemplary embodiment of an oral appliance for use on the lower teeth of a user in accordance with aspects of the present inventions;

FIG. 9D illustrates a bottom view of an exemplary embodiment of the major connector of an oral appliance for use on the lower teeth of a user in accordance with aspects of the present inventions;

Figure 1:
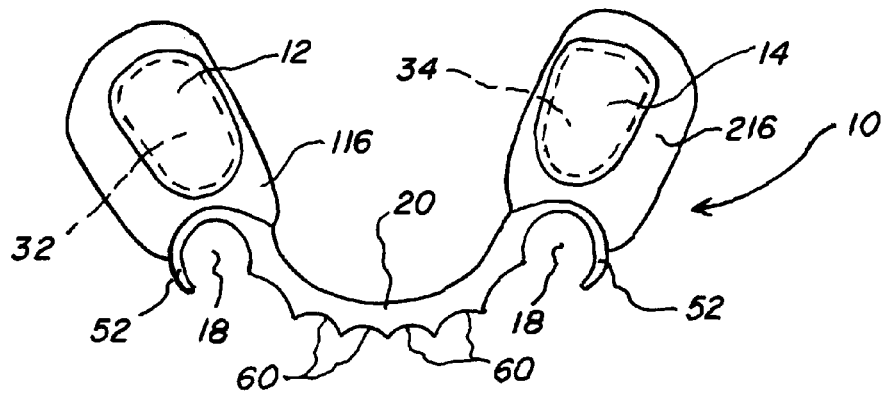
FIG. 1 illustrates a front elevation view of an exemplary embodiment of an oral appliance to be positioned on the upper teeth a user in accordance with aspects of the present inventions.
Figure 2:
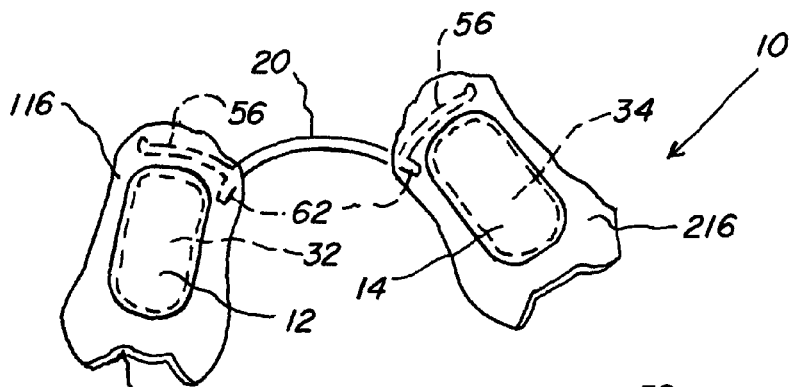
FIG. 2 illustrates a rear elevation view of an exemplary embodiment of an oral appliance to be positioned on the lower teeth of a user in accordance with aspects of the present inventions.

All Figures are illustrated for ease of explanation of the basic teachings of the present invention only; the extensions of the Figures with respect to number, position, relationship and dimensions of the parts to form the embodiment will be explained or will be within the skill of the art after the following description has been read and understood. Further, the exact dimensions and dimensional proportions to conform to specific force, weight, strength, and similar requirements will likewise be within the skill of the art after the following description has been read and understood.

Where used in various Figures of the drawings, the same numerals designate the same or similar parts. Furthermore, when the terms "top," "bottom," "right," "left," "forward," "rearward," "front," "rear," "first," "second," "inside," "outside," "upper," "lower," "inferior," "superior," "anterior," "posterior," "proximal," "distal," "facial," "buccal," "labial," "oral," "lingual," "palatal," "distal," "mesial," and similar positional and/or relative terms are used, the terms should be understood to reference the structures shown in the drawings as they will typically be utilized by one skilled in the art or otherwise as would be recognized by one skilled in the art.

DETAILED DESCRIPTION OF THE INVENTION

The present inventions provide oral appliances 10 and methods for their manufacture. The figures generally illustrate embodiments of oral appliances 10 and methods for their manufacture in accordance with the present inventions. The particular exemplary embodiments of the oral appliances 10 illustrated in the figures have been chosen for ease of explanation and understanding of the various aspects of the present inventions. These illustrated embodiments are not meant to limit the scope of coverage but instead to assist in understanding the context of the language used in this specification and the appended claims. Accordingly, variations of oral appliances 10 including claimed aspects of the inventions different from the illustrated embodiments may be encompassed by the appended claims.

Various embodiments of oral appliances 10 in accordance with aspects of the present invention are illustrated throughout the figures for exemplary purposes. The illustrated oral appliances 10 include at least a first bite pad 12 and a second bite pad 14 interconnected by a major connector 20. The first bite pad 12 may be defined by, secured to, or integral with in a first body 116. Similarly, the second bite pad 14 may be defined by, secured to, or integral with a second body 216. The first body 116 and the second body 216 may be configured to secure and/or position the first bite pad 12 and the second bite pad 14 (collectively, "bite pads 12, 14") at the desired position relative to the occlusal surface of the teeth. In certain aspects, the first body 116 and the second body 216 may each form a channel 18 or at least a portion of a channel 18 to receive the teeth of a user.

The first bite pad 12 includes at least a first spacer 32 and the second bite pad 14 includes at least a second spacer 34. The first bite pad 12 and the second bite pad 14 include a first spacer 32 and a second spacer 34, respectively, formed from a material selected to maintain the separation of the occlusal surfaces of the teeth during clenching or upon impact to the jaw. The bite pads 12, 14 may be configured to space the occlusal surface of one or more premolars and molars when the teeth of a user are clenched and may be generally configured to reduce or alleviate pressure at the temporomandibular joint when the user's teeth are clenched. The bite pads 12, 14 may also or alternatively be generally configured to protect the teeth and/or temporomandibular joint of a user when the user is subject to a blow to the jaw, head or otherwise receives an impacting force that may travel to or through the jaw.

FIGS. 1 to 5 illustrate perspective views of exemplary embodiments of an oral appliance 10 configured to be positioned over the teeth of a user in accordance with aspects of the present inventions. As illustrated, the embodiment of oral appliance 10 may be configured to be received over at least some of the upper teeth or lower teeth of a user. The first body 116 and the second body 216 are interconnected by major connector 20 configured to be positioned against the lingual or palatal surface of the gums. The first body 116 has at least a first bite pad 12 defined as a thickened region of the first body 116 and includes a first spacer 32 to maintain a desired thickness of the first bite pad 12 during clenching or upon an impact to the jaw. The second body 216 has at least a second bite pad 14 defined as a thickened region of the second body 216 and includes a second spacer 34 to maintain a desired thickness of the second bite pad 14 during clenching or upon an impact to the jaw. The first bite pad 12 and the second bite pad 14 are generally configured to be positioned over at least one of the lower molars on each side of a user's jaw when worn by a user. When the upper teeth and the lower teeth of a user are juxtaposed, the first bite pad 12 and the second bite pad 14 may be positioned between at least some of the upper molars and/or premolars and some of the lower molars and/or premolars. In certain embodiments, the first bite pad 12 and the second bite pad 14 may cover at least a portion of the second premolar and at least a portion of the first molar on each side of the jaw of a user.

The major connector 20 secures the first bite pad 12 to the second bite pad 14. In certain embodiments, the major connector 20 may secure the first bite pad 12 to the second bite pad 14 by being secured to the first body 116 and the second body 216 to which the first bite pad 12 and the second bite pad 14 are respectively secured or otherwise integrated. The major connector 20 is typically configured to extend as an arch around the lingual or palatal side of the front teeth of a user. In certain embodiments, the major connector 20 may extend along or just below the gum line on an oral appliance 10 configured for the lower teeth or along or just above on an oral appliance 10 configured for the upper teeth. This positioning of the major connector can reduce the perceived obtrusiveness of the bar within the mouth and can also reduce the impact on a user's speech.

The major connector 20 may take the form of a lingual bar or lingual plate when the oral apparatus 10 is configured to be secured over the lower teeth and may take the form of a palatal bar or palatal plate when the oral apparatus 10 is configured to be secured over the upper teeth. The major connectors may be made from various metals, metal alloys, various polymers, various laminates, various natural materials or other synthetic materials as will be recognized by those skilled in the art upon review of the present disclosure.

The mounting portions 62 may include various features to secure the bodies 116, 216 or the spacers 32, 34 to the major connector 20. The major connectors 20 typically include at least a mounting portion 62 on each side of the major connector 20 to which the first body 116 and second body 216 and/or the first spacer 32 and second spacer 34 may be secured. The mounting portions 62 are typically the portion of the major connector that is covered by materials that forms the bodies 116, 216 or spacers 32, 34. The mounting portions 62 typically include portions that conform to at least one of the teeth or gum line of the user. These portions are typically configured to conform to reduce the obtrusiveness of the oral appliance 10 in the mouth of the user. The conforming portion may include flattened regions to conform to the gums and teeth of a user. The mounting portions 62 may include a textured or otherwise treated surface to assist in the bonding between the material or materials that form the bodies 116, 216 and/or spacers 32, 34 and the material that forms the mounting portion 62 of the major connectors 20. In addition or alternatively, the mounting portions 62 of the major connectors 20 may include one or more mounting passages 64 extending through portions of the mounting portions 62. The mounting passages 64 may receive the material or materials that form the bodies 116, 216 or spacers 32, 34 which may mechanically hold the materials that form the bodies 116, 216 or spacers 32, 34 or may permit the chemical or mechanical bonding of the materials that form the bodies 116, 216 or spacers 32, 34 between which the mounting portion 62 may be secured.

In certain aspects, the major connector 20 may include one or more dental supports 52 positioned near, adjacent or within the first body 116 and the second body 216 and/or the first spacer 32 and second spacer 34. The dental supports 52 may generally comprise a portion of the mounting portion 62 that extends around at least a majority of a single tooth or a cusp of a tooth. The dental supports 52 may be generally configured to laterally stabilize the major connector 20 and associated first body 116 and second body 216 at the desired position within a user's mouth.

In certain aspects, the major connector 20 may include a first dental clasp 56 positioned near, adjacent or within the first body 116 and/or first spacer 32 and a second dental clasp 56 positioned near, adjacent or within the second body 216 and/or second spacer 34. The dental clasps 56 may be generally configured to secure the major connector 20 and associated first body 116 and second body 216 at the desired position within a user's mouth. Typically, the dental clasps 56 are configured to comfortably engage between two teeth by extending around from the lingual to the buccal surfaces of the teeth. In some aspects, a ball may be provided on the distal end of the dental clasp 56 to assist in engagement with the teeth.

In certain embodiments, the major connector 20 may also define one or more dental recesses 60. Each dental recess 60 configured to receive a rear aspect of a tooth within the recess. In certain aspects, the dental recesses may function to smooth the transition between major connector 20 and the teeth of the user to improve comfort and/or to decrease the distraction generated by contacting the major connector 20 with the tongue.

The first body 116 and the second body 216 may be composed of one or more layers of materials. These materials can include ethyl-vinyl acetate (EVA); thermoplastic polyolefin, various ethylene-based elastomers; various hydrocarbon resins (which are may be combined with EVA, thermoplastic polyolefin, or various ethylene-based elastomers), polycaprolactone (which may be combined with EVA), low-density polyethylene, high density poly-ethylene, polycarbonate and/or various polymers, laminates and other materials that will be recognized by those skilled in the art upon review of the present disclosure. In certain aspects, the composite material may be a pre-laminated sheet including a layer of polycarbonate bound to a layer of polyester urethane which is available under the trade name Durasoft® from the Scheu Dental Co. located in Iserlohn, Germany. Typically, these materials are selected with a durometer (hardness) of between 70 A to 96 A or between 55D and 90D.

At least a portion of the inferior surface of the first body 116 and the second body 216 may conform to the shape of the teeth of the user. This can enhance the fit, comfort and retention of the oral appliance 10 in the mouth of a user. At least a portion of a superior surface of the first body 116 and the second body 216 may also be shaped to correspond to the shape of the teeth of a user. In certain aspects, this shape may enhance the comfort and aesthetics of the oral appliance 10. The first body 116 and the second body 216 typically form channels 18 to receive the teeth. The channels 18 are elongated and are generally oriented along the mesial-distal axis. The at least a portion of a channel 18 may extend over one or more of the canines, premolars and/or molars on each side of the mouth. The channel 18 may be configured in shape of the teeth of the user. The channel 18 or the portion of a channel 18 may be defined by the inferior surface of the first body 116 and second body 216 to receive the teeth of the user. A channel occlusal surface 24 contacts at least a portion of the occlusal surface of the teeth. The channel occlusal surface 24 may be configured to conform to a least a portion of the occlusal surface of the user's teeth and may be configured to conform to the surfaces of all of the teeth received in the channel 18. To conform, typically, cavities will be formed in the channel occlusal surface 24 to correspond to at least the cusps of the occlusal surfaces. In certain aspects, this may more evenly distribute the force from clenching or an impact over the occlusal surface of the teeth and, among other things, may also improve retention and fitment.

When the teeth are engaged in the channel 18 in an oral appliance 10 configured to be secured over the lower teeth, a buccal body edge 144 of the first body 116 and second body 216 may extend below the lower gum-line of the user or some or all of the buccal body edge 144 may be configured to extend to a point above the lower gum-line of a user. When the teeth are engaged in the channel 18 in an oral appliance 10 configured to be secured over the upper teeth of a user, the buccal body edge 144 of the first body 116 and second body 216 may extend above the upper gum-line of the user or some or all of the buccal body edge 144 may be configured to extend to a point below the upper gum-line of a user.

The first body 116 and the second body 216 each form a mesial body edge 140. The mesial body edge 140 is typically configured to be positioned at or distal to the canines when the oral appliance is positioned in the mouth of a user. This can reduce the comfort of the device by eliminating coverage of the lingual side of the incisors that can cause irritation to the tongue of users.

The first body 116 and the second body 216 also each form a distal body edge 142. The distal body edge 142 is typically configured to be positioned at or mesial to the second molar or, when present, the third molar when the oral appliance is positioned in the mouth of a user.

At least the portion of the first body 116 and the second body 216 may define the first bite pad 12 and the second bite pad 14 (collectively "bite pads" 12, 14). The bite pads 12, 14 of oral appliance 10 may be configured to at least reduce pressure in the temporomandibular joint as the lower mandible is clenched. In certain aspects, the oral appliance 10 may tend to direct the mandibular condyle downward from the articular fossa in response an attempt by a user to clench their teeth. In other aspects, the oral appliance 10 may tend to direct the mandibular condyle downward and forward from the articular fossa in response an attempt by a user to clench their teeth.

The first bite pad 12 and the second bite pad 14 may be solely include a first spacer 32 and a second spacer 34 (collectively "spacers 32, 34"), respectively. Alternatively, the bite pads 12, 14 may be formed as a composite structure with each bite pad 12, 14 including one or more spacers 32, 34. When the bite pads 12, 14 are formed as a composite structure, the spacers 32, 34 may be embedded or encapsulated within one or more materials forming the bodies 116, 216. As such, the bite pads 12, 14 may include one or more of an outer layer 26 and an inner layer 26 of material secured over one or more spacers 32, 34. The spacers 32, 34 may be positioned between the outer layer 26 and the inner layer 26. The spacers 32, 34 are typically formed from a material having a greater hardness than the material of the outer layer 26 and inner layer 26. The spacers 32, 34 are typically of sufficient hardness to resist substantial penetration by the teeth and deformation as the teeth of a user are clenched. A material such as high density polyethylene or polypropylene may be used as well as other materials that will be recognized by those skilled in the art upon review of the present disclosure. The spacers 32, 34 may have a constant thickness from the front edge to the rear edge of the spacers 32, 34, it may be thicker at the front edge and be tapered to a thinner rear edge, it may have a thinner front edge and be tapered to a thicker rear edge, or it may be otherwise configured as will be recognized by those skilled in the art upon review of the present disclosure.

The bite pads 12, 14 are generally configured to define an external occlusal surface 22 to contact at least a portion of the occlusal surface of the opposing teeth and a channel occlusal surface 24 to contact the occlusal surfaces of the teeth relative to which the oral appliance 10 is secured. At least a portion of the channel occlusal surface 24 is coextensive with the channel occlusal surface 24 and may include the characteristics and features of the channel occlusal surface 24 as described above. The bite pads 12, 14 are generally configured to be positioned adjacent the occlusal surfaces of at least one of the canines, the premolars and the molars with at least one bite pad 12, 14 on each side of a user's mouth. Typically, the bite pads 12, 14 are positioned over the occlusal surfaces of at least one the premolars and at least one of the molars. In other aspects, the bite pads 12, 14 may be solely positioned over the occlusal surfaces of one or more molars.

In various aspects, the spacers 32, 34 of the bite pads 12, 14 may be configured to at least one of guide the mandible into a position that reduces or alleviates pressure at the temporomandibular joint during clenching and/or to transfer at least a portion of the force from an impact to the jaw to the cranium through the maxilla. The spacers 32, 34 are typically formed from a material having a sufficient hardness to resist substantial deformation when the teeth of a user are clenched while in contact with the spacer 32, 34. Accordingly, the spacers 32, 34 typically will have a durometer of between about 60D to about 90D although this may vary in certain embodiments of the invention.

Typically, the spacers 32, 34 are configured to be generally coextensive with the bite pads 12, 14. From a top view, the spacers 32, 34 may have an oblong shape and can be generally rectangular shape, a kidney shape, an oval shape, an egg shape or be otherwise shaped to extend along at least a portion of an occlusal surface of the underlying teeth as will be recognized by those skilled in the art upon review of the present disclosure. The spacers 32, 34 may define a mesial edge 40, a distal edge 42, a buccal edge 44, a lingual edge 46, a spacer channel surface 48, and a spacer outer surface 50. The spacers 32, 34 are generally configured to space the occlusal surface of opposing teeth when a clenching force is exerted by the user. For purposes of the present description, the length of the spacers 32, 34 extends between a mesial edge 40 and a distal edge 42 of the spacers 32, 34, the width of the spacers 32, 34 extends between a buccal edge 44 and a lingual edge 46 of the spacer, and the thickness of the spacers 32, 34 extends along the spacer channel surface 48 and an spacer channel surface 48 of the spacers 32, 34. Depending upon the particular application and particular products design, the length of the spacers 32, 34 is typically between about 10 millimeters to about 25 millimeters. The width of the spacers 32, 34 may be selected to contact or otherwise provide support between opposing teeth. The spacers 32, 34 are typically at least as wide as the distance between the cusps of individual adjacent teeth and the cusps of the opposing teeth. In certain aspects, the width may be as wide or wider than the width of the adjacent teeth or at least as wide as the spacing of the cusps of the teeth. Typically, they will be between about 5 millimeters and 15 millimeters. The thickness of the spacers 32, 34 generally establishes the distance the teeth will remain separated when the jaw is clenched or upon impact. The thickness of the spacers 32, 34 is typically between 0.25 millimeter and 2.5 millimeters. However, the spacers 32, 34 may have a constant thickness, a decreasing thickness along its length, or have their thickness otherwise varied along their length and/or width to reduces or alleviates pressure at the temporomandibular joint during clenching and/or to transfer at least a portion of the force from an impact to the jaw to the cranium through the maxilla. In certain aspects, the spacers 32, 34 may be configured as wedges with a thickness at their mesial ends that may approach 0.00 millimeters and a thickness at their distal ends between 0.25 millimeter and 2.5 millimeters. However, the mesial edge 40 of wedge shaped spacers 32, 34 typically has a thickness of at least 0.20 millimeters and the thickness at their distal ends of between 0.50 millimeters and 2.00 millimeters.

Figure 6A:
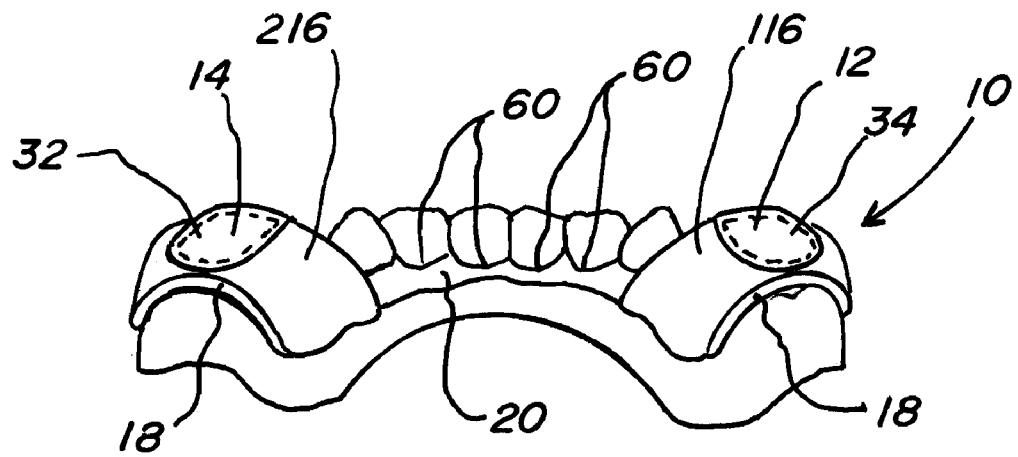
FIG. 6A illustrates a rear view of an exemplary embodiment of an oral appliance positioned on the lower teeth of a user in accordance with aspects of the present inventions.
Figure 6B:
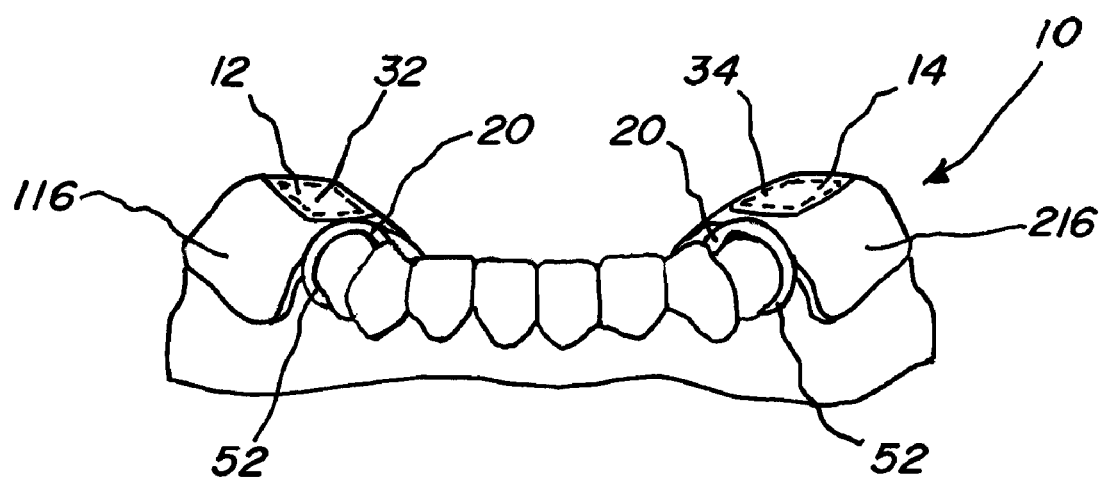
FIG. 6B illustrates a front view of an exemplary embodiment of an oral appliance positioned on the lower teeth of a user in accordance with aspects of the present inventions.
Figure 6C:
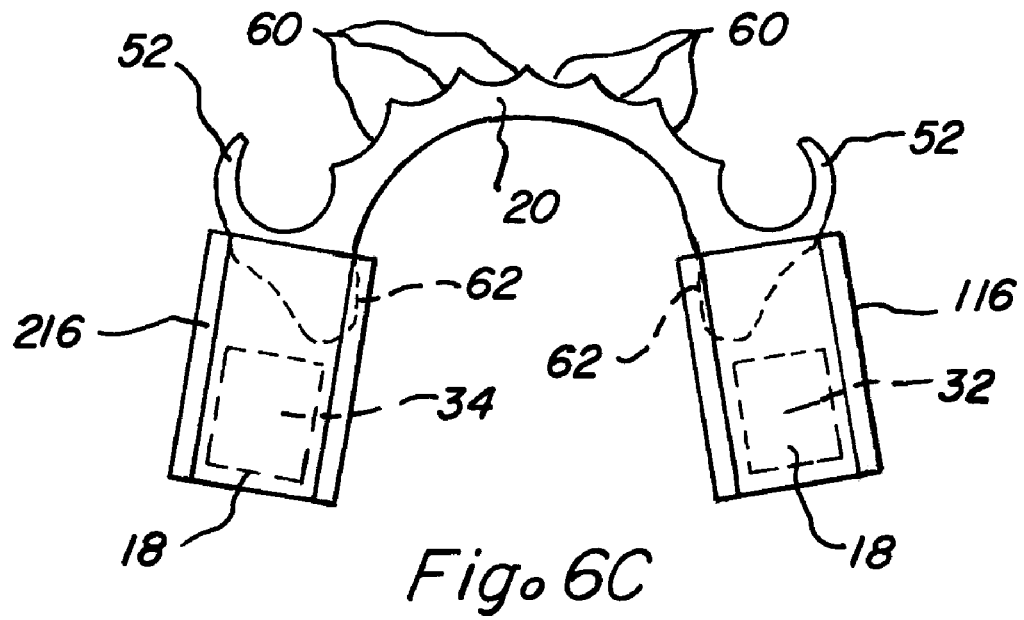
FIG. 6C illustrates a bottom view of an exemplary embodiment of an oral appliance for use on the lower teeth of a user in accordance with aspects of the present inventions.
Figure 6D:
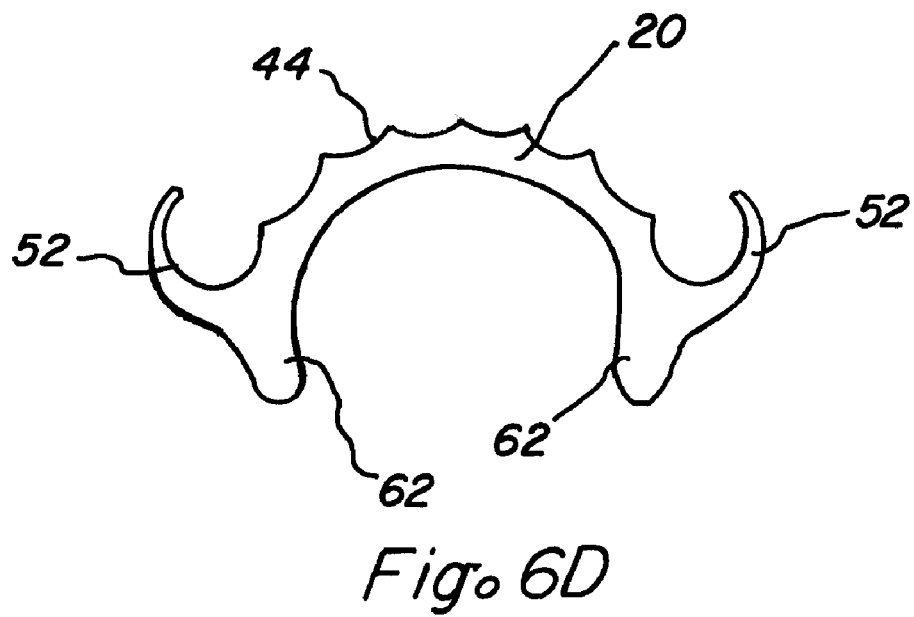
FIG. 6D illustrates a bottom view of an exemplary embodiment of the major connector of an oral appliance for use on the lower teeth of a user in accordance with aspects of the present inventions.

FIGS. 6A and 6B illustrate a rear view and a front view, respectively, of an oral appliance 10 similar to that of FIG. 1 positioned on the lower teeth of a user. As illustrated, one or more molars and premolars are positioned within the channel 18 defined by each of the first body 116 and the second body 216. The major connector 20 extends above the gum line to receive the rear portions of at least the canines and incisors in the dental recesses 60 defined at the front edge of the major connector 20. FIG. 6C illustrates the major connector 20 and its mounting portions 62 configured to be secured within the first body 116 and the second body 216. In addition, the relative position of the first spacer 32 and the second spacer 34 are illustrated in phantom within the first body 116 and the second body 216, respectively. FIG. 6D illustrates a bottom view of the major connector 20 formed as a unitary structure for exemplary purposes.

Figure 3:
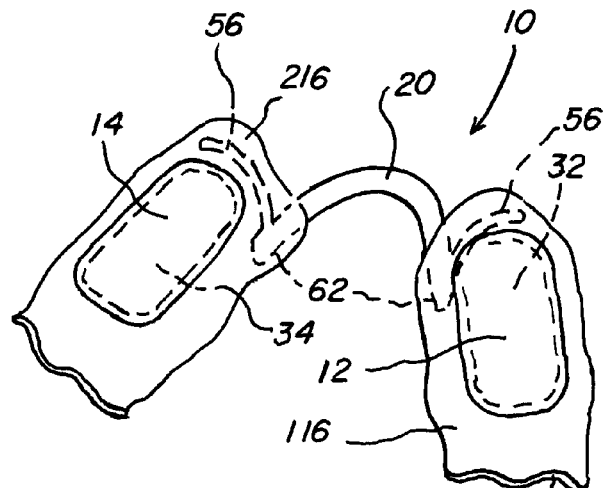
FIG. 3 illustrates a rear elevation view of an exemplary embodiment of an oral appliance to be positioned on the lower teeth of a user in accordance with aspects of the present inventions.
Figure 7A:
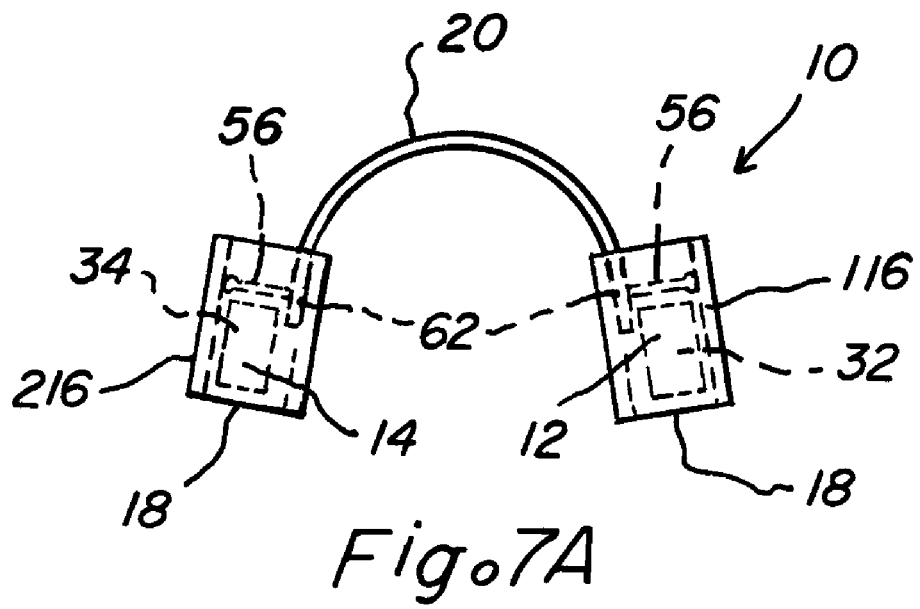
FIG. 7A illustrates a bottom view of another exemplary embodiment of an oral appliance positioned on the lower teeth of a user in accordance with aspects of the present inventions.
Figure 7B:
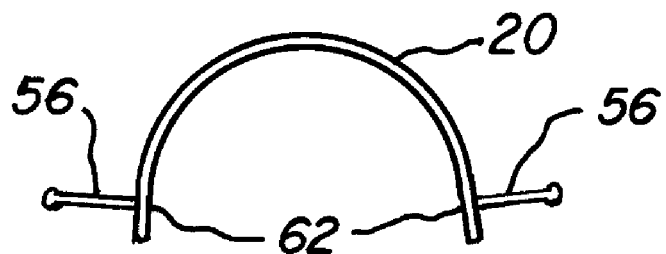
FIG. 7B illustrates a bottom view of an exemplary embodiment of the major connector of an oral appliance for use on the lower teeth of a user in accordance with aspects of the present inventions.
Figure 7C:
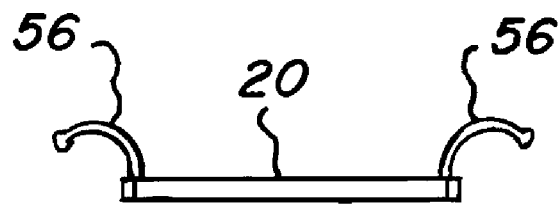
FIG. 7C illustrates a rear view of an exemplary embodiment of the major connector of an oral appliance for use on the lower teeth of a user in accordance with aspects of the present inventions.

FIGS. 7A and 7C illustrate another embodiment of a major connector 20 of an oral appliance similar to that of FIG. 3. As illustrated in FIG. 7A, the major connector 20 and its mounting portions 62 configured to be secured within the first body 116 and the second body 216 and/or first spacer 32 and second spacer 34. These figures also illustrate the dental clasps 40 extending from the major connector 20 in an arch configured to conform to and extend around a gap between two teeth to secure the major connector 20 and the associated first body 116 and second body 216 and/or first spacer 32 and second spacer 34 at a desired position in the mouth of a user. In addition, the dental clasp 56 is configured as a ball clasp with a ball at the end of each dental clasp 56 to assist in securing the major connector 20 and the associated first body 116 and second body 216 at a desired position in the mouth of a user.

Figure 4:
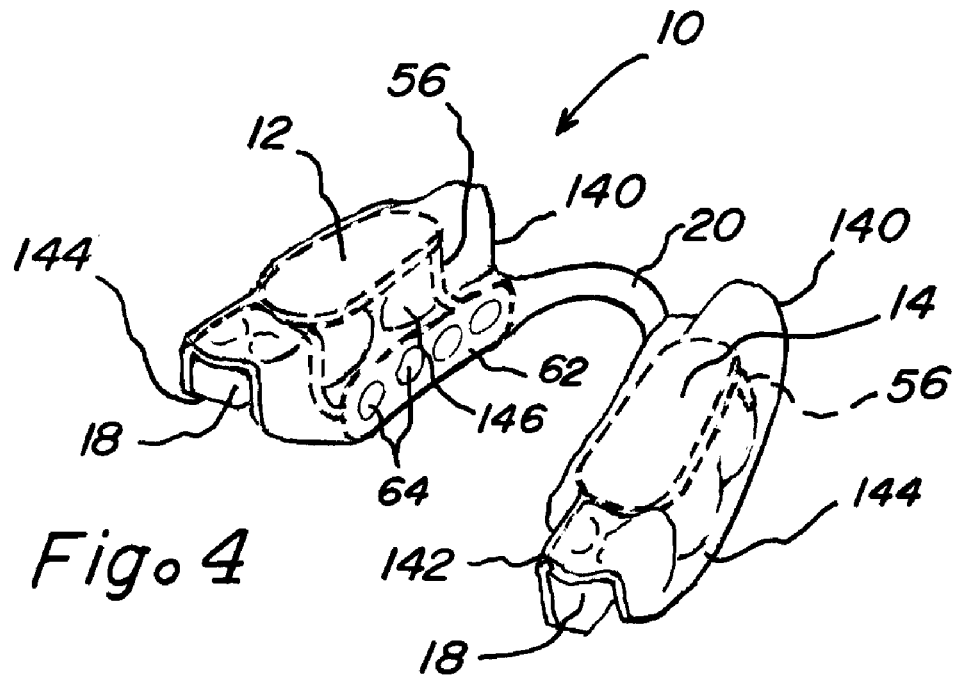
FIG. 4 illustrates a rear elevation view of an exemplary embodiment of an oral appliance to be positioned on the lower teeth of a user in accordance with aspects of the present inventions.
Figure 8A:
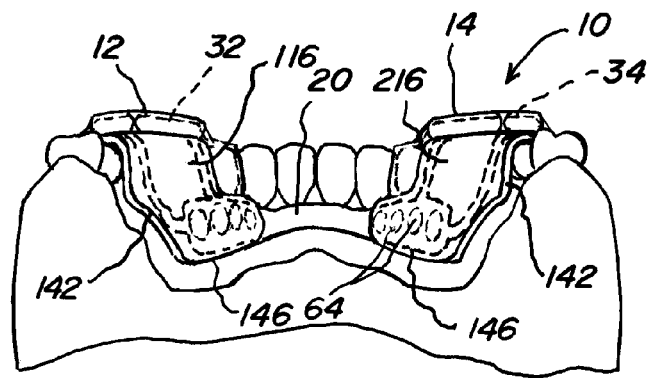
FIG. 8A illustrates a rear view of an exemplary embodiment of an oral appliance positioned on the lower teeth of a user in accordance with aspects of the present inventions.
Figure 8B:
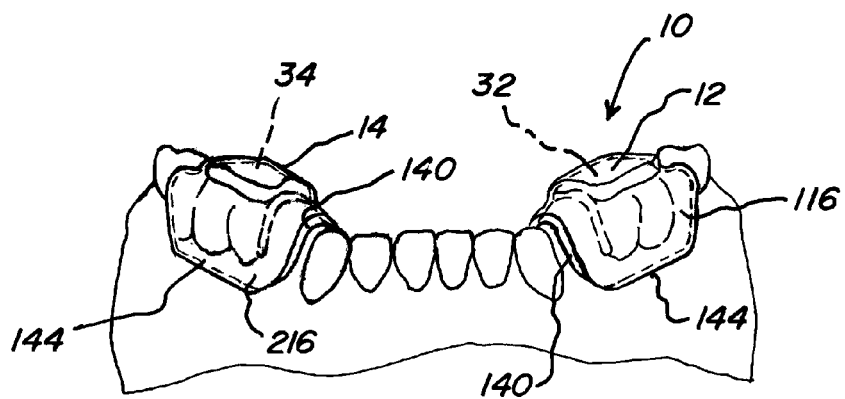
FIG. 8B illustrates a front view of an exemplary embodiment of an oral appliance positioned on the lower teeth of a user in accordance with aspects of the present inventions.

FIGS. 8A and 8B illustrate a rear view and a front view, respectively, of an oral appliance 10 similar to that of FIG. 4 positioned on the lower teeth of a user. As illustrated, one or more molars and premolars are positioned within the channel 18 defined by each of the first body 116 and the second body 216. The major connector 20 extends around the front of the mouth along the lingual surface of the gums just under the gum line. The major connector 20 extends mesial from the mesial body edges 140 of the first body 116 and the second body 212 and forms an arch 72 of the major connector 20 at or below the gum line of a user. This positioning can improve the comfort and/or reduce impediments to the speech of a user. In certain embodiments, the arch 72 may be substantially coplanar in a transverse plane defined at one or more points along the lingual body edge 146 of the first body 116 and the second body 216. In certain embodiments configured for use on the lower teeth, the arch 72 may be positioned above a transverse plane defined at one or more points along the lingual body edge 146 of the first body 116 and the second body 216. In embodiments configured for use on the upper teeth, the arch 72 may be positioned below a transverse plane defined at one or more points along the lingual body edge 146 of the first body 116 and the second body 216. A distal first dental clasp 56 and a mesial first dental clasp 56 are secured within the first body 116. The distal first dental clasp 56 is secured between the first and second molars and a mesial first dental clasp 56 is secured between the first and second premolars for exemplary purposes. A distal second dental clasp 56 and a mesial second dental clasp 56 are secured within the second body 216.

The mesial body edge 140 of the first body 116 is positioned at mesial of the first premolar and the distal body edge 142 of the first body 116 is positioned at distal of the second molar to position the first body 116 between at least the first premolar and second molar for exemplary purposes. Similarly, the mesial body edge 140 of the second body 216 is positioned at mesial of the first premolar and the distal body edge 142 of the second body 216 is positioned at distal of the second molar to position the second body 216 between at least the first premolar and second molar for exemplary purposes. The distal second dental clasp 56 is secured between the first and second molars and a mesial second dental clasp 56 is secured between the first and second premolars for exemplary purposes. The mesial edge 40 of the first spacer 32 is positioned over the mesio-occlusal surface of the second premolar and the distal edge 42 of the first spacer 32 is positioned at about the disto-occlusal surface of first molar on the left side of the mouth for exemplary purposes. The mesial edge 40 of the second spacer 34 is positioned over the mesio-occlusal surface of the second premolar and the distal edge 42 of the second spacer 34 is positioned at about the disto-occlusal surface of first molar on the right side of the mouth for exemplary purposes.

Figure 8C:
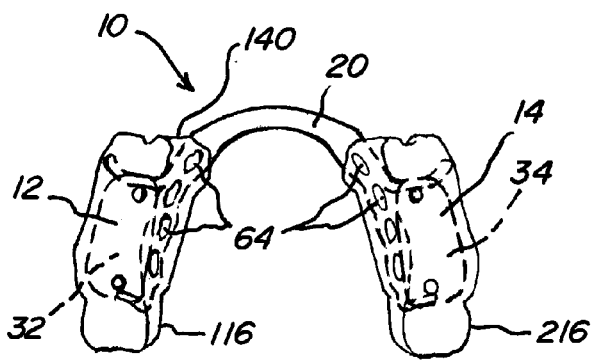
FIG. 8C illustrates a bottom view of an exemplary embodiment of an oral appliance for use on the lower teeth of a user in accordance with aspects of the present inventions.
Figure 8D:
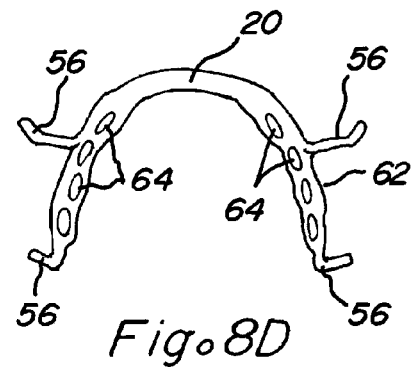
FIG. 8D illustrates a bottom view of an exemplary embodiment of the major connector of an oral appliance for use on the lower teeth of a user in accordance with aspects of the present inventions.

FIG. 8C illustrates a top view of an oral appliance 10 with the major connector 20 and its mounting portions 62 secured within the first body 116 and the second body 216. In addition, the relative position of the first spacer 32 and the second spacer 34 are illustrated in phantom within the first body 116 and the second body 216, respectively. FIG. 8D illustrates a top view of the major connector 20 formed as a unitary structure for exemplary purposes. As illustrated, the mounting portion 62 of the major connector 20 includes a labial plate 74. The labial plate 74 generally lies parallel to the underlying tissue surface of a user. The labial plate 74 is configured to secure the major connector 20 relative to the gums of a user. The labial plate 74 may define one or more mounting passages 64 to further secure the first body 116 and second body 216 to the labial plate 74 of the mounting portion 62.

Figure 5:
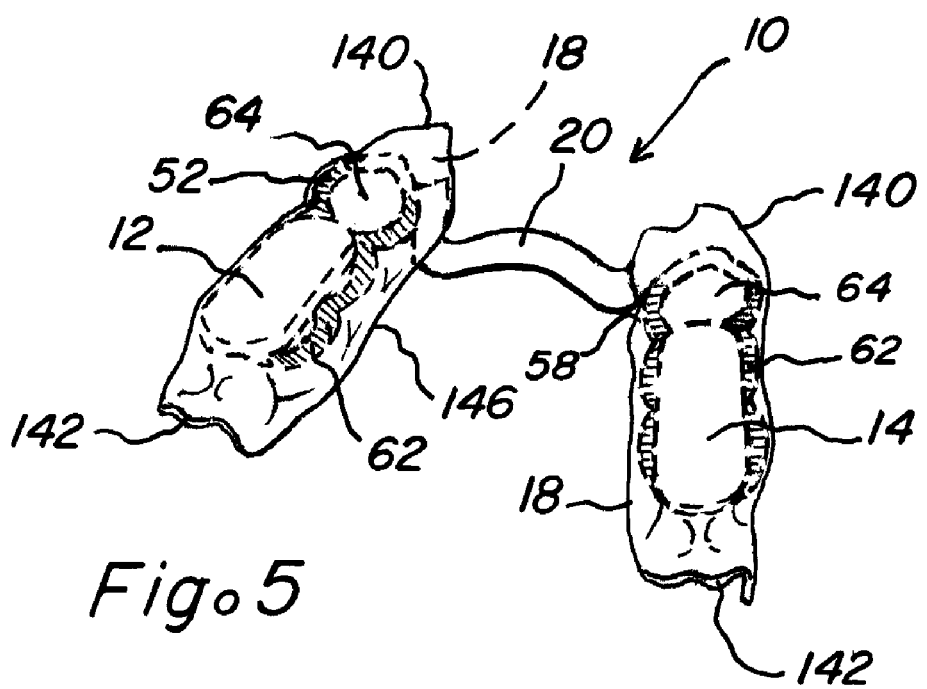
FIG. 5 illustrates a rear elevation view of an exemplary embodiment of an oral appliance to be positioned on the lower teeth of a user in accordance with aspects of the present inventions.

FIGS. 9A and 9B illustrate a rear view and a front view, respectively, of an oral appliance 10 similar to that of FIG. 5 positioned on the lower teeth of a user. As illustrated, one or more canines, molars and premolars are positioned within the channel 18 defined by each of the first body 116 and the second body 216.

The major connector 20 extends around the front of the mouth along the lingual surface of the gums just under the gum line. The major connector 20 extends away from lingual body edges 146 of the first body 116 and the second body 216 toward or through a transverse plane defined at one or more points along the lingual body edges 146. The major connector 20 further includes a mesial bend 70 to position an arch 72 of the major connector 20 at or below the gum line of a user. This positioning can improve the comfort and/or reduce impediments to the speech of a user. In certain embodiments, the arch 72 may be positioned substantially coplanar in a transverse plane defined at one or more points along the lingual body edge 146 of the first body 116 and the second body 216. In certain embodiments configured for use on the lower teeth, the arch 72 may be positioned below a transverse plane defined at one or more points along the lingual body edge 146 of the first body 116 and the second body 216. In embodiments configured for use on the upper teeth, the arch 72 may be positioned above a transverse plane defined substantially at the lingual body edge 146 of the first body 116 and the second body 216.

A distal first dental support 52, an intermediate first dental support 52 and a mesial first dental support 52 of the major connector 20 are secured within the first body 116. The distal first dental support 52 is secured above the major bulge of the first molar, the intermediate first dental support 52 is secured above the major bulge of the second premolar, and the mesial first dental support 52 is secured above the major bulge of the first premolar on the left side of the mouth for exemplary purposes. A distal second dental support 52, an intermediate second dental support 52 and a mesial second dental support 52 are secured within the second body 216. The distal second dental support 52 is secured above the major bulge of the first molar, the intermediate second dental support 52 is secured above the major bulge of the second premolar, and the mesial second dental support 52 is secured above the major bulge of the first premolar on the right side of the mouth for exemplary purposes. One or more dental supports 52 can form a crown mount 76 type mounting structure of the mounting portion 63 of the major connector 20 which is configured to relatively secure the major connector to at least the crowns of a user's teeth.

The mesial body edge 140 of the first body 116 is positioned mesial of the canine and the distal body edge 142 of the first body 116 is positioned mesial of the second molar to position the first body 116 between at least the first premolar and second molar for exemplary purposes. Similarly, the mesial body edge 140 of the second body 216 is positioned mesial of the canine and the distal body edge 142 of the second body 216 is positioned mesial of the second molar to position the second body 216 between at least the canine and second molar for exemplary purposes. The mesial edge 40 of the first spacer 32 is positioned over the mesio-occlusal surface of the second premolar and the distal edge of the first spacer 32 is positioned at about the disto-occlusal surface of first molar on the left side of the mouth for exemplary purposes. The mesial edge 40 of the second spacer 34 is positioned over the mesio-occlusal surface of the second premolar and the distal edge of the second spacer 34 is positioned at about the disto-occlusal surface of first molar on the right side of the mouth for exemplary purposes. FIG. 9C illustrates a top view of an oral appliance 10 with the major connector 20 and its mounting portions 62 secured within the first body 116 and the second body 216. In addition, the relative position of the first spacer 32 and the second spacer 34 are illustrated in phantom within the first body 116 and the second body 216, respectively. FIG. 9D illustrates a top view of the major connector 20 formed as a unitary structure for exemplary purposes. A textured surface of the mounting portion 62 to facilitate adhesion of the material of the first body 116 and second body 216 is illustrated for exemplary purposes.

Figure 10A:
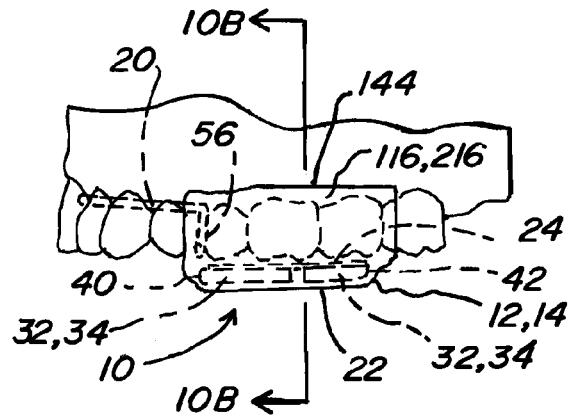
FIG. 10A illustrates a side view of an exemplary embodiment of an oral appliance positioned on the upper teeth of a user in accordance with aspects of the present inventions.

FIG. 10A illustrates a side view of an exemplary embodiment of an oral appliance positioned on the upper teeth of a user. The oral appliance 10 is secured over the upper teeth of a user with a channel 18 that extends over the disto-occlusal of the second premolar to the mesio-occlusal of the second molar. The channel occlusal surface 24 is shown configured to conform to the shape of the occlusal surface of the upper teeth. As illustrated, the bite pad 12, 14 includes spacers 32, 34 positioned within the first body 116 and second body 216. The illustrated spacers 32, 34 have a thicker rear edge that tapers to a thinner front edge for exemplary purposes. Further, the bite pads 32, 34 are formed as two separate components that cooperate to form a wedge shaped bite pad 32, 34 for exemplary purposes. The dental clasp 56 extends lingual to buccal from the major connector 20 to between the groove between second premolar and the first molar. The ball of the dental clasp 56 contacts a buccal aspect of the second premolar and the first molar to further secure the major connector 20 and the associated first body 116 and second body 216 at the desired position. The major connector 20 extends around the lingual (palatal) side of the incisors, canines and first premolar for exemplary purposes.

Figure 10B:
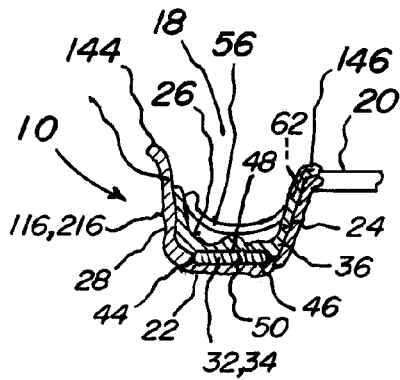
FIG. 10B illustrates a cross section through section 10B-10B of the oral appliance of FIG. 3A illustrating the composite structure.

FIG. 10B illustrates a cross section through section 10B-10B of the oral appliance of FIG. 10A illustrating the composite structure of this portion of the oral appliance 10. The channel 18 is shown extending downward from a buccal body edge 144 of the body 116, 216 and around to the lingual body edge 146. The inner surface of channel 18 as illustrated is shaped to correspond with the profile of at least a portion of the teeth of a user. The inner shape may at least in part be formed in the inner material 36 which in the illustrated embodiment forms the inner layer 26 of the composite structure of the bite pad 32, 34 and/or body 116, 216. The channel occlusal surface 24 is shaped to conform to the occlusal surfaces of the adjacent teeth. More particularly, the portion of the inner material 36 which defines the channel occlusal surface 24 is shaped to receive the occlusal surface of a molar. Similarly, the external occlusal surface 22 is shaped to receive at least a portion of the occlusal surfaces of the adjacent teeth. Among other things, this internal shaping may improve one or more of comfort, retention and shock/force dispersion. The outer surface the buccal wall and lingual wall of the outer layer 28 may be shaped to correspond to the shape of the underlying teeth which may improve comfort and the aesthetics of some embodiments.

The inner material 36 of the inner layer 26 may be secured to the outer material 38 of the outer layer 28 along at least a portion of the lingual wall and at least a portion of the buccal wall and along other portions of the body 116, 216 where the inner material 36 of the inner layer 26 and the outer material 38 of the outer layer 28 come into contact. In various aspects, the materials 36, 38 of the layers 26, 28 may be heat fused, chemically linked, adhesively bonded, mechanically interconnected or otherwise secured to one another as will be recognized by those skilled in the art upon review of the present disclosure. At least a portion of the inner material 36 of the inner layer 26 in the lower portion of the channel 18 is at least in part positioned against and in some embodiments secured to spacer channel surface 48 of the spacers 32, 34. At least a portion of the outer layer 26 defining the channel occlusal surface 22 is positioned against and in some embodiments secured to a spacer outer surface 50 of the spacer 32, 34. In various aspects, the materials 36, 38 of the layers 26, 28 may be heat fused, chemically linked, adhesively bonded, mechanically interconnected or otherwise secured to the spacer surfaces 48, 50 as will be recognized by those skilled in the art upon review of the present disclosure. The spacers 32, 34 may be encapsulated between or otherwise secured to or within the inner materials 36 of the inner layer 26 and the outer material 38 of the outer layer 38 which form the bodies 116, 216 of the oral appliance 10. At least a portion of the mounting portion 62 of the major connector 20 is secured between the inner layer 26 and the outer layer 28 with the dental clasp 56 extending through in the inner layer 26 for exemplary purposes. Various other structures of the mounting portion 62 of the major connector 20 may extend into, through and between one or more layers 26, 28 of the bodies 116, 216 and into and through the spacers 32, 34 to secure the major connector relative to these elements.

Figure 10C:
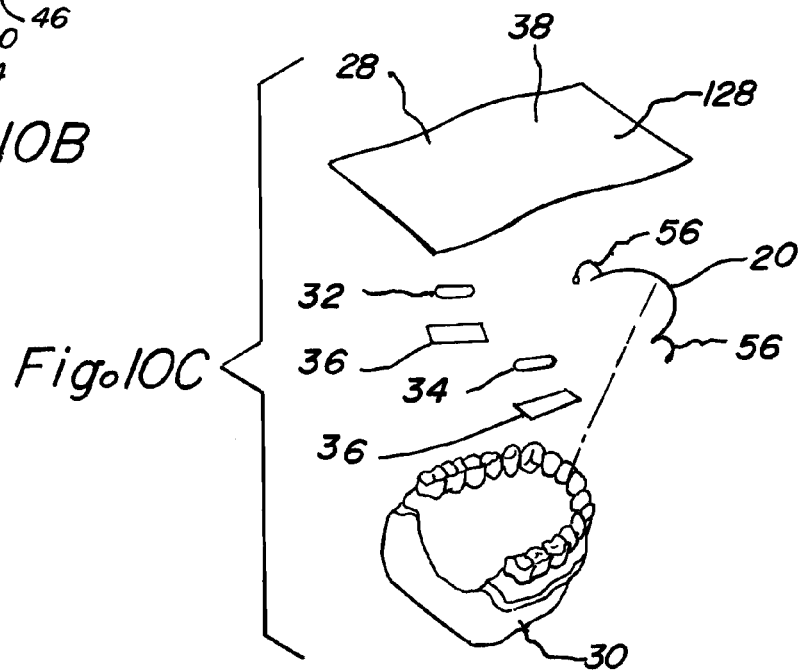
FIG. 10C illustrates an exploded perspective view exemplary embodiments of the components of the oral appliance as the components are assembled during manufacture in accordance with aspects of the present inventions.

FIG. 10C illustrates an exploded perspective view an exemplary embodiment of the components of the oral appliance 10 as the components may be assembled during manufacture. As illustrated, the method includes configuring and assembling at least an inner material 36, a pair of spacers 32, 34 and an outer blank 128 to form an oral appliance 10. The components may also include a major connector 20. For each oral appliance 10, a model 30 of upper or lower teeth over which the oral appliance 10 will be formed is provided. The model 30 is typically formed by casting liquid stone or plaster in an impression of the upper or lower teeth of a user or into a standardized mold. The various components are positioned over the model 30 and the outer blank 128 if formed over the model 30 and associated components to the interconnected components may then have the excess materials removed to produce an oral appliance 10.

In one step, the inner material 36 which will form the inner layer 26 over at least a portion of the channel occlusal surface 24 of the channel 18 is positioned on the model 30. Typically, the inner material 36 is placed over at least one or more of the canines, premolars, and molars of the model 30. The material 36 may be temporarily secured to the model by softening it with heat, by press fitting it onto the model 30 or otherwise as will be recognized by those skilled in the art depending on the material being used. The inner material 36 may be in a solid or a liquid form and may be a material such as one of various EVA based adhesives, various uncured polymers, various heat softening polymers, various light curable polymers or other materials as will be recognized by those skilled in the art upon review of the present disclosure. The inner material 36 is positioned at a desired location on the model 30. Typically, the inner material 36 is positioned on at least a portion of the occlusal surfaces of one or more of the molars and premolars. In certain embodiments, the inner material 36 is positioned on at least a portion of the occlusal surfaces at least the second premolar and the first molar of the model 30. The inner material 36 is generally selected and/or prepared to be formable over the teeth of model 30 as the outer blank 128 is made to conform to the model 30. It is desirable that the inner material 36 may satisfy the comfort and durability requirements for an inner surface of an oral appliance 10 as will be recognized by those skilled in the art upon review of the present disclosure. The inner material 36 may at least in part be selected to stabilize the position of the spacer 32, 34 on one or more of the molars and/or premolars of the model during manufacture.

The spacers 32, 34 are positioned at the desired location on an upper surface of or otherwise over the inner material 36. In certain aspects, the spacers 32, 34 may be secured at the desired location on or in the inner material 36. The spacer channel surface 48 of the spacers 32, 34 is positioned against the inner material 36. The inner material 36 may be made or may be provided as soft or tacky because of being a chemically treated, uncured, heated or softened or may have other properties or configurations to enable the spacers 32, 34 to be positioned relative to inner material 36 during manufacture as will be recognized by those skilled in the art upon review of the present disclosure. Prior to during or after, the positioning of the spacers 32, 34, the major connector 20 may be positioned on the model 30 and the mounting portion 62 is positioned relative to the spacers 32, 34 and inner material 36 to facilitate their cooperation in securing the major connector 20 if required by the particular design of the oral appliance 10. In certain designs, the major connector 20 may alternatively secured to the other components at after the outer blank 128 is formed over the model 30 or after the excess material from the forming step has been removed.

A pressure forming apparatus 100 may be provided. The pressure forming apparatus 100 is generally configured to exert a force over a surface of the outer blank 128 to form it over the model 30 and associated components of the oral appliance 10. As will be recognized by those skilled in the art, a wide range of pressure forming apparatus may be used to form the outer blank 128 over the model 30 and may be applicable to the present methods. By way of non-limiting examples, the pressure forming apparatus 100 may be one or more of various devices for providing pneumatic pressure, hydraulic pressure, mechanical pressure or may use other forces to form the outer blank 128 to over the model 30 and associated components of the oral appliance 10.

Figure 10D:
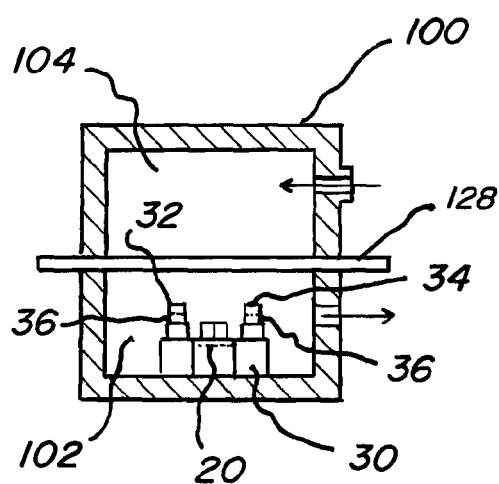
FIG. 10D illustrates a cross section of an exemplary embodiment of an outer blank positioned to be formed over a model of an individual's dentition in accordance with aspects of the present inventions.
Figure 10E:
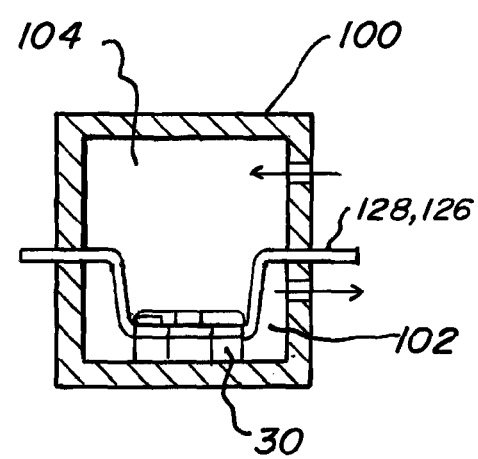
FIG. 10E illustrates a cross section of an exemplary embodiment of an outer/inner blank positioned being formed over a model of an individuals dentition in accordance with aspects of the present inventions.

As illustrated for exemplary purposes in FIGS. 10D and 10E, the model 30 is placed in a forming chamber 102 of a pressure forming apparatus 100 that uses pneumatic pressure to form the outer blank 128 over the model. The outer blank 128 of the outer material 38 desired to form the outer layer 26 is provided. When the outer material 38 is an EVA for example, the outer blank 128 may have a thickness from about 1.0 millimeters to about 6.0 millimeters and is typically between about 1.8 millimeters to about 4.0 millimeters. When the outer material 38 is a sheet of composite material including laminated an upper layer of polycarbonate and a lower layer of polyester urethane (the lower layer to be positioned against the teeth), the outer blank 128 may have a thickness of between about 1.0 millimeter and 6.0 millimeters with a typical thickness dimension being 0.8 mm of polycarbonate material and 1.0 millimeters of polyester urethane. The outer blank 128 is secured in the pressure forming apparatus 100 to sealingly separate the forming chamber 102 from a high pressure chamber 104. The temperature of the outer blank 128 and/or the forming chamber 102 and high pressure chamber 104 as well as the model 30 may be raised to soften the outer blank 128. A pressure gradient is then generated between the high pressure chamber 104 and the forming chamber 102 to deform the outer blank 128 and force at least a portion of the outer blank 128 into the forming chamber 102 and against the spacer 38, at least some of the inner material 36 and the model 30. Among other methodologies, the pressure gradient may be formed by increasing the pressure in the high pressure chamber 102 or forming at least a partial vacuum in the forming chamber 102. The temperatures and pressure differential may be selected to secure the outer blank 128 to the inner material 36 where they come into contact. Similarly, the temperatures and pressure differential may be selected to secure the outer blank 128 and/or the inner material 36 to the spacer 32, 34 where they come into contact with the spacer 32, 34. In certain embodiments, the temperature and pressure are configured to fuse the materials of at least two of the outer blank 128, the inner material 36 and the spacer 32, 34. As the outer blank 128 is forced against the model 30 in the forming chamber 102, a lower surface of the outer blank 128 conforms to the shape of the spacers 32, 34, the model 30, and, to some degree, depending upon its formulation and state, the inner material 36. The major connector 20 may be secured to the oral appliance 10 prior to or subsequent to placement of the model 30 in the pressure forming apparatus 100. In methods where the major connector 20 is secured at this step, the major connector may be secured in or between one or more of the outer blank 128, the spacers 32, 34 and the inner material 36. In certain aspects, the major connector 20 may be secured in a desired position relative to the model 30 such that the mounting portion 62 is or will be positioned within or on at least one of the inner material 36 and material of the outer blank 128 or otherwise secured at the desired position in each of the first body 116 and the second body 216. As will be noted by those skilled in the art upon review of the present disclosure, various chemical treatments, adhesives, or other components may be integrated into the components or positioned between the layers to improve or alter the securing, bonding, connecting, linking and/or integration of the various components of the oral appliance 10.

After the over-molding process, the oral appliance 10 is removed from the model 30 and may be trimmed of excess material. In addition, the oral appliance 10 may be mounted on an articulator and heated to form an impression of the opposing teeth on the surface opposite the cavity 18. Alternatively, the oral appliance 10 may be heated and manually articulated to form an impression of the opposing teeth on the surface opposite the cavity 18.

Figure 11A:
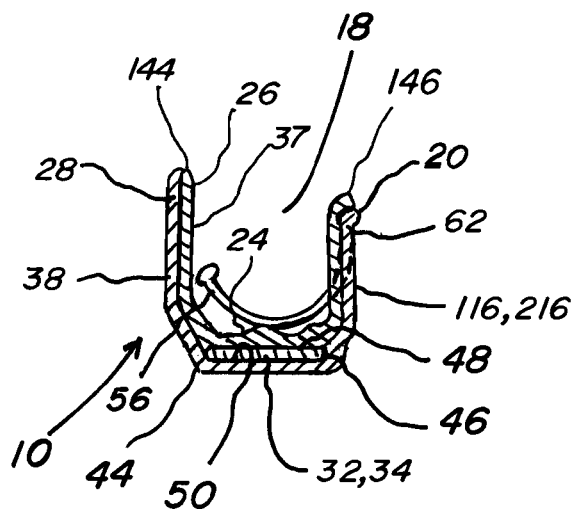
FIG. 11A illustrates a cross section through section 6B-6B of the oral appliance of FIG. 4A illustrating the composite structure.

FIG. 11A illustrates a cross section through section 10B-10B of an oral appliance 10 of similar configuration of that shown in FIG. 10A. The channel 18 is shown extending downward from the buccal body edge 144 of the bodies 116, 216 and around to the lingual body edge 146. The inner layer 26 of channel 18, as illustrated, is shaped to correspond with the profile of at least portions of the teeth of a user. The inner shape may at least in part be formed in the inner sheet material 37 which in the illustrated embodiment forms the inner layer 26 of the composite structure of the bite pad 32, 34 and/or body 116, 216. The channel occlusal surface 24 is shaped to conform to the occlusal surfaces of the adjacent teeth. More particularly, the portion of the inner sheet material 37 which defines the channel occlusal surface 24 is shaped to receive the occlusal surface of a molar. Similarly, the external occlusal surface 22 is shaped to receive at least a portion of the occlusal surfaces of the adjacent teeth. Among other things, this internal shaping may improve one or more of comfort, retention and shock/force dispersion. The outer surface the buccal wall and lingual wall of the outer layer 28 may be shaped to correspond to the shape of the underlying teeth which may improve comfort and the aesthetics of some embodiments.

The inner sheet material 37 of the inner layer 26 may be secured to the outer material 38 of the outer layer 28 along at least a portion of the lingual wall and at least a portion of the buccal wall and along other portions of the body 116, 216 where the inner material 36 of the inner layer 26 and the outer material 38 of the outer layer 28 come into contact. In various aspects, the materials 37, 38 of the layers 26, 28 may be heat fused, chemically linked, adhesively bonded, mechanically interconnected or otherwise secured to one another as will be recognized by those skilled in the art upon review of the present disclosure. When present, an inner material 36 may be provided between at least a portion of one or more of the inner layer 26 and the outer layer 28. At least a portion of the inner sheet material 37 of the inner layer 26 in the lower portion of the channel 18 may be at least in part positioned against and in some embodiments secured to spacer channel surface 48 of the spacers 32, 34. In embodiments utilizing an inner material 36, the inner material 36 may be provided between at least a portion of one or more of the inner layer 26 and the spacer channel surface 48 of the spacers 32, 34. At least a portion of the outer layer 26 defining the channel occlusal surface 22 may be positioned against and in some embodiments secured to a spacer outer surface 50 of the spacer 32, 34. In various aspects, the materials 37, 38 of the layers 26, 28 may be heat fused, chemically linked, adhesively bonded, mechanically interconnected or otherwise secured to the spacer surfaces 48, 50 as will be recognized by those skilled in the art upon review of the present disclosure. The spacers 32, 34 may be encapsulated between or otherwise secured to or within the inner sheet material 37 of the inner layer 26 and the outer material 38 of the outer layer 38 which form the bodies 116, 216 of the oral appliance 10. At least a portion of the mounting portion 62 of the major connector 20 is secured between the inner layer 26 and the outer layer 28 with the dental clasp 56 extending through in the inner layer 26 for exemplary purposes. Various other structures of the mounting portion 62 of the major connector 20 may extend into, through and between one or more layers 26, 28 of the bodies 116, 216 and into and through the spacers 32, 34 to secure the major connector relative to these elements.

Figure 11B:
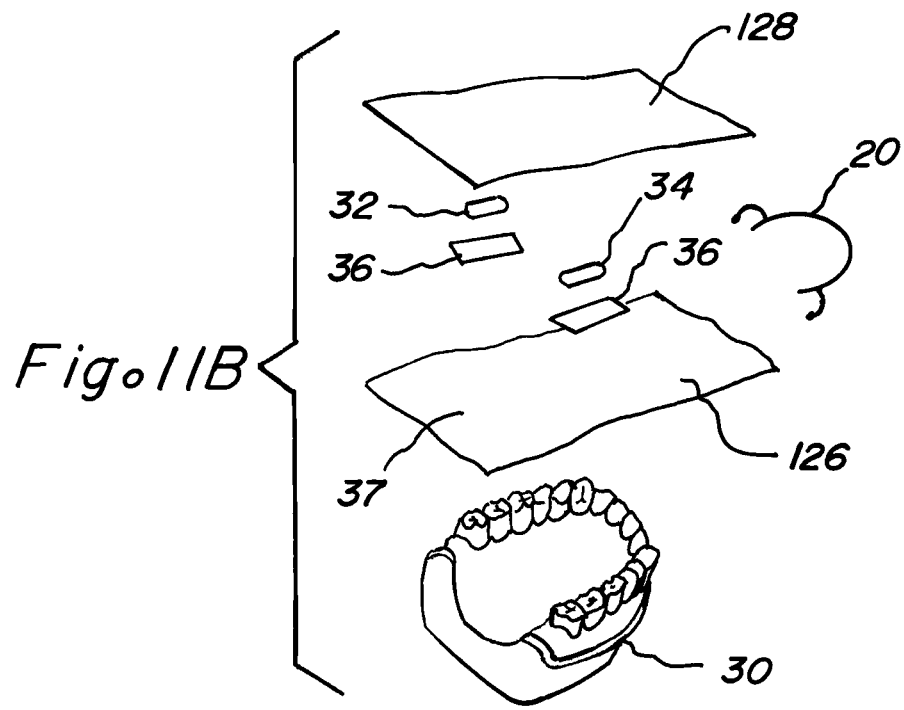
FIG. 11B illustrates an exploded perspective view exemplary embodiments of the components of the oral appliance as the components are assembled during manufacture in accordance with aspects of the present inventions.

FIG. 11B illustrates an exploded perspective view of other exemplary embodiments of the components of the oral appliance 10 as the components may be assembled during manufacture. As illustrated, the method includes configuring and assembling at least an outer blank 128, a pair of spacers 32, 34, and an inner blank 126 to form an oral appliance 10. The components may also include an inner material 36 and a major connector 20. For each oral appliance 10, a model 30 of upper or lower teeth over which the oral appliance 10 will be formed is provided. The model 30 is typically formed by casting liquid stone or plaster in an impression of the upper or lower teeth of a user or into a standardized mold. Initially, the inner blank 126 is formed over the model 30. The various components are positioned over the formed inner blank 126 on the model 30 and the outer blank 128 if formed over the model 30 and associated components to the interconnected components may then have the excess materials removed to produce an oral appliance 10.

In one step, the model 30 is placed in a forming chamber 102 of a pressure forming apparatus 100 (as generally illustrated for exemplary purposes in FIGS. 10A and 10D). An inner blank 126 of the material desired to form the inner layer 26 is provided. When the material is EVA, the inner blank 126 may have a thickness from about 1.0 millimeters to about 6.0 millimeters and is typically between 0.8 millimeters to about 4.0 millimeters in thickness. The inner blank 126 is secured in the pressure forming apparatus 100 to sealingly separate the forming chamber 102 from a high pressure chamber 104. The temperature of the inner blank 126 and/or the forming chamber 102 and high pressure chamber 104 as well as the model 30 may be raised to soften the inner blank 126. A pressure gradient is then generated between the high pressure chamber 104 and the forming chamber 102 to deform the inner blank 126 and force at least a portion of the inner blank 126 into the forming chamber 102 and against the model 30. As the inner blank 126 is forced against the model 30 in the forming chamber 102, a lower surface and, to varying degrees, an upper surface, of the inner blank 126 conforms to the shape of the model 30.

In another step, the inner material 36 may be positioned over the portion of the inner blank 126 onto which the spacers 32, 34 are to be secured. The inner material 36 may function to secure the spacers 32, 34 at the desired location on the model 30 during manufacture. As such, the inner material 36 may be placed on the inner blank 126 over at least one or more of the canines, premolars, and molars of the model 30 over at least a portion of the area on which the spacers 32, 34 will be secured. The inner material 36 may at least in part be selected to stabilize the position of the spacer 32, 34 on the inner blank 126 over the occlusal surfaces of one or more of the molars and/or premolars of the model 30 during manufacture.

The spacers 32, 34 are positioned at the desired location on an upper surface of or otherwise positioned over of the inner blank 126 and/or, when present, the inner material 36. In certain aspects, the spacers 32, 34 may be secured at the desired location on or in the inner material 36. The spacer channel surface 48 of the spacers 32, 34 is positioned against the inner blank 126 and/or, when present, the inner material 36. Prior to during or after, the positioning of the spacers 32, 34, the major connector 20 may be positioned on the model 30 and the mounting portion 62 is positioned relative to the spacers 32, 34 and the inner blank 126 and/or, when present, the inner material 36 to facilitate their cooperation in securing the major connector 20 if required by the particular design of the oral appliance 10. In certain designs, the major connector 20 may alternatively secured to the other components at after the outer blank 128 is formed over the model 30 or after the excess material from the forming step has been removed.

The molded inner blank 126 and associated components are then positioned in the forming chamber 102 under the outer blank 128 as illustrated generally in FIGS. 10D and 10E. When the outer material 38 is an EVA for example, the outer blank 128 may have a thickness from about 1.0 millimeters to about 6.0 millimeters and typically has a thickness between about 1.8 millimeters to about 4.0 millimeters. The outer blank 128 is secured in the pressure forming apparatus 100 to sealingly separate the forming chamber 102 from a high pressure chamber 104. The temperature of the outer blank 128 and/or the forming chamber 102 and high pressure chamber 104 as well as the model 30 may be raised to soften the outer blank 128. A pressure gradient is then generated between the high pressure chamber 104 and the forming chamber 102 to deform the outer blank 128 and force at least a portion of the outer blank 128 into the forming chamber 102 and against the spacers 32, 34, at least some of the inner material 36 and the model 30. Among other methodologies, the pressure gradient may be formed by increasing the pressure in the high pressure chamber 102 or forming at least a partial vacuum in the forming chamber 102. The temperatures and pressure differential may be selected to secure the outer blank 128 to the inner blank 126 and/or, when present, the inner material 36 where they come into contact. Similarly, the temperatures and pressure differential may be selected to secure the outer blank 128 and/or the inner blank 126 and/or, when present, the inner material 36 to the spacer 32, 34 and/or, they come into contact with the spacer 32, 34. In certain embodiments, the temperature and pressure are configured to fuse the materials of at least two of the outer blank 128, the inner blank 126 and the spacer 32, 34. As the outer blank 128 is forced against the inner blank 126 and in the forming chamber 102, a lower surface of the outer blank 128 conforms to the shape of the spacers 32, 34, the inner blank 126 and/or, to some degree, depending upon its formulation and state, the inner material 36 when present. The major connector 20 may be secured to the oral appliance 10 prior to or subsequent to placement of the model 30 in the pressure forming apparatus 100. In methods where the major connector 20 is secured at this step, the major connector may be secured in or between one or more of the outer blank 128, the spacers 32, 34, the inner blank 126 and, when present, the inner material 36. In certain aspects, the major connector 20 may be secured in a desired position relative to the model 30 such that the mounting portion 62 is or will be positioned within or on at least one of the inner sheet material 37 of the inner blank 126, the outer material 38 of the outer blank 128 or otherwise secured at the desired position in each of the first body 116 and the second body 216. As will be noted by those skilled in the art upon review of the present disclosure, various chemical treatments, adhesives, or other components may be integrated into the components or positioned between the layers to improve or alter the securing, bonding, connecting, linking and/or integration of the various components of the oral appliance 10.

After the over-molding process, the oral appliance 10 is removed from the model 30 and may be trimmed of excess material. In addition, the oral appliance 10 may be mounted on an articulator and heated to form an impression of the opposing teeth on the surface opposite the cavity 18. Alternatively, the oral appliance 10 may be heated and manually articulated to form an impression of the opposing teeth on the surface opposite the cavity 18.

The foregoing discussion discloses and describes merely exemplary embodiments of the present invention. Upon review of the specification, one skilled in the art will readily recognize from such discussion, and from the accompanying drawings and claims, that various changes, modifications and variations can be made therein without departing from the spirit and scope of the invention as defined in the following claims.

What is claimed is:

1. An oral appliance, comprising:
a first body configured to be secured over one or more teeth of a user, the first body comprising a composite structure, the composite structure comprising at least an outer layer secured over an inner layer, the first body further defining at least a first bite pad comprising at least a first spacer secured between the outer layer and the inner layer, the first bite pad in a position to contact at least one of a molar and a premolar of a user, an inner surface of the inner layer defining an exterior shape of the teeth of the user, the first spacer defining a spacer outer surface and a spacer channel surface with at least a portion of at least one of the spacer outer surface and the spacer channel surface having a substantially planar configuration and the first spacer formed from a material having a durometer of at least 60D to resist substantial deformation and retaining a substantially planar configuration between at least two cusps of the teeth of the user when the teeth of the user are clenched;

a second body configured to be secured over one or more teeth of a user, the second body comprising a composite structure, the composite structure comprising at least an outer layer secured over an inner layer, the second body further defining at least a second bite pad, the composite structure at the second bite pad comprising at least a second spacer secured between the outer layer and the inner layer, the second bite pad in a position to contact at least one of a molar and a premolar of a user, an inner surface of the inner layer defining an exterior shape of the teeth of the user, the second spacer defining a spacer outer surface and a spacer channel surface with at least a portion of at least one of the spacer outer surface and the spacer channel surface having a substantially planar configuration and the first spacer formed from a material having a durometer of at least 60D to resist substantial deformation and retaining a substantially planar configuration between at least two cusps of the teeth of the user when the teeth of the user are clenched;

a major connector defining a first mounting portion and a second mounting portion, the first mounting portion secured to the first body and the second mounting portion secured to the second body.

2. An oral appliance, as in claim 1, comprising the major connector extending from a buccal edge of the first body and having a first mesial bend and the major connector extending from a buccal edge of the second body and having a second mesial bend, an arch of the major connector extending between the firs mesial bend and the second mesial bend with the first mesial bend and the second mesial bend configured to position the arch of the major connector adjacent to at least one of the incisors of the user and the gum line adjacent to the incisors of the user.

3. An oral appliance, as in claim 1, comprising the major connector extending from a mesial edge of the first body and the major connector extending from a buccal edge of the second body, an arch of the major connector extending between the first body and the second body with the arch of the major connector adjacent to at least one of the incisors of the user and the gum line adjacent to the incisors of the user.

4. An oral appliance, as in claim 1, comprising the first spacer comprising a mesial end having a thickness that is less than a thickness a distal end and the second spacer comprising a mesial end having a thickness that is less than a thickness a distal end.

5. An oral appliance, as in claim 1, comprising the first spacer comprising a substantially uniform thickness between a mesial end and a distal end of the first spacer, and the second spacer comprising a substantially uniform thickness between a mesial end and a distal end of the second spacer.

6. An oral appliance, as in claim 1, comprising the first spacer comprising a varied thickness between a mesial end and a distal end, and the second spacer comprising a varied thickness between a mesial end and a distal end.

* * * * *